(12) United States Patent
Miyake et al.

(10) Patent No.: US 9,845,273 B2
(45) Date of Patent: Dec. 19, 2017

(54) METHOD FOR PRODUCING CHLOROHYDROCARBON HAVING CONJUGATED DOUBLE BONDS

(71) Applicant: Shin-Etsu Chemical Co., Ltd., Tokyo (JP)

(72) Inventors: Yuki Miyake, Joetsu (JP); Takeshi Kinsho, Joetsu (JP); Miyoshi Yamashita, Joetsu (JP); Naoki Ishibashi, Joetsu (JP); Takehiko Fukumoto, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/189,373

(22) Filed: Feb. 25, 2014

(65) Prior Publication Data

US 2014/0275657 A1 Sep. 18, 2014

(30) Foreign Application Priority Data

Mar. 14, 2013 (JP) .................. 2013-051712

(51) Int. Cl.
C07C 17/16 (2006.01)
C07C 17/07 (2006.01)

(52) U.S. Cl.
CPC .............. C07C 17/07 (2013.01); C07C 17/16 (2013.01)

(58) Field of Classification Search
CPC ...................................................... C07C 17/16
See application file for complete search history.

(56) References Cited

U.S. PATENT DOCUMENTS

| 2,837,574 | A | * | 6/1958 | Hill et al. ............... 568/614 |
| 3,872,172 | A | | 3/1975 | Bertele et al. |
| 6,737,236 | B1 | * | 5/2004 | Pieken .................. C07C 271/22 424/193.1 |

FOREIGN PATENT DOCUMENTS

| JP | 05-213779 | 8/1993 |
| JP | 2000-086547 | 3/2000 |

OTHER PUBLICATIONS

Fortin, S. et al. J. Am. Chem. Soc. 2001, 123, 8210-8216.*
Fortin, D. et al. Tetrahedron 2001, 57, 4167-4177.*
Kapferer (Kapferer, T. et al. Eur. J. Org. Chem. 2006, pp. 2119-2133).*
Tashiro, T. et al. Tetrahedron: Asymmetry 2008, 19, pp. 1215-1223.*
Tius, M. A. et al. J. Am. Chem. Soc. 1986, 108, pp. 1035-1039.*
Clough, J. M. et al. "Stereocontrolled Synthesis of Conjugated Polyene Isoprenoids Using Phosphine Oxide Anion Intermediates" Tetrahedron 1981, 37, 3911-3920.*
Binns et al. "The Preparation and Electrocyclic Ring-opening of Cyclobutenes: Stereocontrolled Approaches to Substituted Conjugated Dienes and Trienes", *Tetrahedron* 52(10):3631-3658 (1996).
Caussanel et al. "Comparative Effects of Conjugated and Deconjugated Isomeric Enones on the Transannular Diels—Alder Reaction", *Organic Letters* 5(25):4799-4802 (2003).
Gayral et al. "A Protocol for the Direct Conversion of Aldehydes into Arenes—Proof of Principle", *Synlett* 18:2823-2826 (2007).
Japanese Office Action for Japanese Patent Application No. 2014-051735, Dispatch dated Aug. 5, 2016, 6 pages.
Charoenying, P. et al. "A New Stereocontrolled, Pyrylium-Based Route to Conjugated Dienyes: The First Synthesis of Carduusyne A", *Tetrahedron Letters*, 1996, 37(11), pp. 1913-1916.
Mayr, H. et al. *Tetrahedron*, 1986, 42(24), pp. 6657-6662.

\* cited by examiner

*Primary Examiner* — Medhanit W Bahta
(74) *Attorney, Agent, or Firm* — Myers Bigel, P.A.

(57) ABSTRACT

Provided is a method for producing a chlorohydrocarbon having conjugated double bonds by stereoselectively chlorinating an alcohol having conjugated double bonds. More specifically, provided is a method for producing a chlorohydrocarbon having conjugated double bonds, the method including a step of chlorinating an alcohol having conjugated double bonds with a chlorinating agent in a solvent in the presence of a base and in the absence of metal salt for chlorination of the alcohol, and the alcohol being represented by the formula (1):

$$RCH=CHCH=CH-Z-OH \quad (1)$$

wherein R represents a hydrogen atom or a linear, branched or cyclic $C_{1-17}$ monovalent hydrocarbon group which may have at least one double bond or at least one triple bond; and Z represents a linear, branched or cyclic $C_{1-17}$ divalent hydrocarbon group which may have at least one double bond or at least one triple bond.

1 Claim, No Drawings

METHOD FOR PRODUCING CHLOROHYDROCARBON HAVING CONJUGATED DOUBLE BONDS

RELATED APPLICATION

This application claims priority from Japanese Patent Application No. 2013-051712, filed Mar. 14, 2013, the disclosure of which is incorporated by reference herein in its entirety.

FIELD AND BACKGROUND OF THE INVENTION

The present invention relates to a method for producing a chlorohydrocarbon having conjugated double bonds.

A chlorohydrocarbon having conjugated double bonds can be prepared by chlorinating an alcohol having conjugated double bonds. Use of thionyl chloride or the like which is a common reagent for chlorination, however, accelerates isomerization of conjugated double bonds, leading to a reduction in the purity of an intended product. As another chlorinating method, there is, for example, a method comprising the steps of mesylating the hydroxyl group of an alcohol with methanesulfonyl chloride in the presence of 2,4,6-collidine in an N,N-dimethylformamide solution and then chlorinating the resulting product with lithium chloride (Y. L. Dory et al., 2003, Org. Lett., 5(25), 4799-4802 and C. J. Wallis et al., 1996, Tetrahedron, 52(10), 3631-3658 (1996)). There is also a method comprising a step of chlorinating the hydroxyl group of an alcohol with methanesulfonyl chloride in the presence of triethylamine in a methylene chloride solution (J. M. Brown et al., Synlett., 18, 2823-2826 (2007)).

SUMMARY OF THE INVENTION

However, both of the methods proposed by Y. L. Dory et al. and C. J. Wallis et al. use an expensive metal salt such as lithium chloride in an equivalent amount or more so that they are not suited for industrial production. The method proposed by J. M. Brown et al. is limited to the substrate of allyl alcohol having high reactivity, and is more inferior in yield. Moreover, this method uses methylene chloride having a high environmental load and toxicity as a solvent so that it is not suited for industrial production.

With the foregoing in view, the invention has been made. An object of the invention is to provide a method comprising a step of stereoselectively chlorinating an alcohol having conjugated double bonds to produce a chlorohydrocarbon having conjugated double bonds at a low cost.

It has been found that a chlorohydrocarbon having conjugated double bonds can be produced by chlorinating an alcohol having conjugated double bonds with a chlorinating agent in a solvent in the presence of a base, leading to the completion of the invention.

In the invention, there is provided a method for producing a chlorohydrocarbon having conjugated double bonds, the method comprising a step of chlorinating an alcohol having conjugated double bonds with a chlorinating agent in a solvent in the presence of a base and in the absence of metal salt for chlorination of the alcohol, the alcohol being represented by the formula (1):

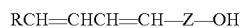

$$RCH=CHCH=CH-Z-OH \quad (1)$$

wherein R represents a hydrogen atom or a linear or branched $C_{1-17}$, or a cyclic $C_{3-17}$, monovalent hydrocarbon group which may have at least one double bond or at least one triple bond; and Z represents a linear or branched $C_{1-17}$, or a cyclic $C_{3-17}$, divalent hydrocarbon group which may have at least one double bond or at least one triple bond.

According to the invention, an expensive metal salt for chlorination of alcohol is not required so that a chlorohydrocarbon having conjugated double bonds can be mass-produced stereoselectively at a low cost. The metal salt used for chlorination of alcohol, which is not required in the invention, includes an alkali metal chloride, an alkaline earth metal chloride, and a chloride or a complex chloride of transition metal or the like, and examples thereof include lithium chloride, nickel chloride, magnesium chloride, sodium chloride, titanium tetrachloride and dilithium tetrachlorocuprate.

DETAILED DESCRIPTION OF THE PREFERRED EMBODIMENTS

The present invention now will be described more fully hereinafter in which embodiments of the invention are provided with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. Unless otherwise defined, all technical and scientific terms used herein have the same meaning as commonly understood by one of ordinary skill in the art to which this invention belongs. All references cited are incorporated herein by reference in their entirety.

According to the invention, in the chlorination reaction, an alcohol having conjugated double bonds and being represented by the formula (1): $RCH=CHCH=CH-Z-OH$ is chlorinated with a chlorinating agent in a solvent in the presence of a base to form a chlorohydrocarbon having conjugated double bonds and being represented by the formula (2): $RCH=CHCH=CH-Z-Cl$.

The compound represented by the formula (1) has cis-trans isomers of the double bond so that alcohols having conjugated double bonds and being represented by the following formulas (3) to (6) may exist as the compound. The compound represented by the formula (1) is at least one isomer selected from the group consisting of the isomers represented by the formulas (3) to (6). It may be a pure geometric isomer of any one of them, or a mixture of two to four geometric isomers. It is typically a mixture of four geometric isomers represented by the formulas (3) to (6), respectively, so that chlorohydrocarbons represented by the following formulas (7) to (10) can be obtained.

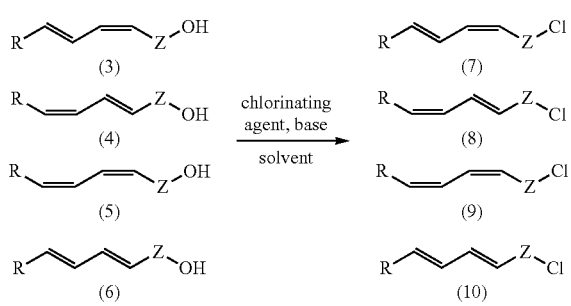

According to the invention, the chlorination reaction is stereoselective so that isomerization of conjugated double bonds in the step of chlorination can be reduced. When the alcohol is a mixture of some geometric isomers, the alcohol can be chlorinated without greatly changing a composition ratio of the mixture. When the alcohol is composed of one geometric isomer, conversion into another isomer can be reduced. For example, isomerization can be reduced to less than 10%, preferably 5% or less, more preferably 3% or less.

R represents a hydrogen atom, or a linear, branched or cyclic monovalent hydrocarbon group having from 1 to 17 carbon atoms, preferably from 1 to 7 carbon atoms, and may have at least one double bond or at least one triple bond.

Examples of R, when it has neither a double bond nor a triple bond, include linear hydrocarbon groups such as methyl, ethyl, propyl, butyl, pentyl, hexyl, decyl, tetradecyl and hexadecyl; branched hydrocarbon groups such as isopropyl, tert-butyl and 2-ethylhexyl; and cyclic hydrocarbon groups such as cyclopropyl, cyclohexyl and cyclooctyl. Examples of R, when it has at least one double bond, include hydrocarbon groups having one to four double bonds such as vinyl, allyl, hexenyl, nonenyl, hexadienyl, heptadienyl, nonadienyl, nonatrienyl, undecatrienyl and dodecatetraenyl. Examples of R, when it has at least one triple bond, include hydrocarbon groups having a triple bond such as propynyl, butynyl, pentynyl and hexynyl.

Z represents a linear, branched or cyclic divalent hydrocarbon group having from 1 to 17 carbon atoms, preferably from 1 to 8 carbon atoms, and may have at least one double bond or at least one triple bond.

Examples of Z, when it has neither a double bond nor a triple bond, include linear alkylene groups such as methylene, ethylene, hexylene, decylene and tetradecylene; branched alkylene groups such as methylethylene and 1-methylpropylene; and cycloalkylene groups such as cyclopropylene, cyclopentylene, cyclohexylene and cyclooctylene. Examples of Z, when it has at least one double bond, include unsaturated alkylene groups having from 1 to 4 double bonds such as vinylene, allylene, hexenylene, nonenylene, hexadienylene, heptadienylene, nonadienylene, nonatrienylene, undecatrienylene and dodecatetraenylene. Examples of R, when it has at least one triple bond, include hydrocarbon groups having a triple bond such as propynylene, butynylene, pentynylene and hexynylene.

Specific examples of the compound represented by the formula (1) include 7,9-dodecadien-1-ol, 9,11-tetradecadien-1-ol, 8,10-dodecadien-1-ol, 3,5-pentadecadien-1-ol, 4,6-hexadecadien-1-ol, 3,5-heptadecadien-1-ol, and 3,5-octadien-1-ol and 9,11-tetradecadien-1-ol.

Examples of the chlorinating agent include sulfonyl chlorides such as benzenesulfonyl chloride, p-toluenesulfonyl chloride and methanesulfonyl chloride. Methanesulfonyl chloride is particularly preferred from the standpoint of reactivity. The chlorinating agent is used in an amount of preferably from 1.0 to 1.8 mol per mol of the alcohol having conjugated double bonds. When the amount is less than 1.0 mol, the reaction may not proceed smoothly. When the amount is more than 1.8 mol, some of the chlorinating agent may be wasted.

Examples of the base include tertiary amines such as tributylamine and N,N-diisopropylethylamine; aromatic amines such as N,N-dimethylaniline and N,N-diethylaniline; 5-membered nitrogen-containing aromatic heterocyclic compounds such as imidazole and pyrrole; and 6-membered nitrogen-containing aromatic heterocyclic compounds such as pyridines including pyridine and collidine. Pyridine, N,N-dimethylaniline, N,N-diethylaniline and N,N-diisopropylethylamine are particularly preferred from the standpoint of reactivity. Depending on the base used, the degree of isomerization of the double bond can be selected. The base can be used in an amount of preferably from 1.0 to 2.6 mol per mol of the alcohol having conjugated double bonds. When the amount is less than 1.0 mol, the reaction may not proceed smoothly. When the amount is more than 2.6 mol, some of the base may be wasted.

Examples of the solvent include hydrocarbon-based solvents such as toluene and hexane; ether-based solvents such as tetrahydrofuran; and polar solvents such as N,N-dimethylformamide, N,N-dimethylacetamide, acetonitrile and dichloromethane. N,N-dimethylformamide and N,N-dimethylacetamide are preferred from the standpoint of reactivity. The solvent can be used in an amount of preferably from 100 to 500 g per mol of the alcohol having conjugated double bonds. When the amount is less than 100 g, the reaction may not proceed smoothly. When the amount is more than 500 g, some of the solvent may be wasted and an amount of the reactants may have to be reduced.

EXAMPLES

The invention will hereinafter be described specifically based on Examples. However, it should not be construed that the invention is limited to or by the Examples, Example 1

The 7,9-dodecadien-1-ol (EZ/EE/(ZE+ZZ)=84.6/14.2/1.2, 36.46 g, 0.200 mol) comprising mainly an (E,Z) isomer, pyridine (28.48 g, 0.360 mol) and N,N-dimethylformamide (60 g) were placed in a reaction vessel and stirred at 5 to 10° C. for 30 minutes. After stirring, methanesulfonyl chloride (32.07 g, 0.280 mol) was added dropwise thereto at 5 to 15° C. After completion of the dropwise addition, the reaction mixture was stirred at 60 to 65° C. for 2 hours. Then, water (100 g) was added to the reaction mixture to terminate the reaction thereof. Hexane (100 g) was added thereto to separate the reaction mixture into phases. The organic phase was washed with hydrochloric acid and then with an aqueous sodium bicarbonate solution, and concentrated by removal of the solvent under reduced pressure. The residue was then distilled under reduced pressure to obtain 1-chloro-7,9-dodecadiene (EZ/EE/(ZE+ZZ)=83.4/14.6/2.0, 35.14 g, 0.175 mol) mainly in an (E,Z) form. The yield was 87.7%. The isomerization of conjugated double bonds was suppressed to about 1%. The structure was determined by nuclear magnetic resonance spectrum and mass spectrum.

Example 2

The 7,9-dodecadien-1-ol (EZ/EE/(ZE+ZZ)=84.6/14.2/1.2, 36.46 g, 0.200 mol) comprising mainly an (E,Z) isomer, N,N-diisopropylethylamine (46.53 g, 0.360 mol) and N,N-dimethylformamide (60 g) were placed in a reaction vessel, and stirred at 5 to 10° C. for 30 minutes. After stirring, methanesulfonyl chloride (32.07 g, 0.280 mol) was added dropwise thereto at 5 to 15° C. After completion of the dropwise addition, the reaction mixture was stirred at 60 to 65° C. for 2 hours. Then, water (100 g) was added to the reaction mixture to terminate the reaction thereof. Hexane (100 g) was added thereto to separate the reaction mixture into phases. The organic phase was washed with hydrochloric acid and then with an aqueous sodium bicarbonate solution, and concentrated by removal of the solvent under reduced pressure. The residue was distilled under reduced pressure to obtain 1-chloro-7,9-dodecadiene (EZ/EE/(ZE+ZZ)=76.1/20.2/3.7, 32.31 g, 0.161 mol) mainly in an (E,Z) form. The yield was 80.4%. The isomerization of conjugated double bonds was suppressed to about 8%. The structure was determined by nuclear magnetic resonance spectrum and mass spectrum.

Example 3

The 7,9-dodecadien-1-ol (EZ/EE/(ZE+ZZ)=84.6/14.2/1.2, 36.46 g, 0.200 mol) comprising mainly an (E,Z) isomer, N,N-dimethylaniline (43.62 g, 0.360 mol) and N,N-dimethylformamide (60 g) were placed in a reaction vessel, and stirred at 5 to 10° C. for 30 minutes. After stirring, methanesulfonyl chloride (32.07 g, 0.280 mol) was added dropwise thereto at 5 to 15° C. After completion of the dropwise addition, the reaction mixture was stirred at 60 to 65° C. for 2 hours. Then, water (100 g) was added to the reaction mixture to terminate the reaction thereof. Hexane (100 g) was added thereto to separate the reaction mixture into phases. The organic phase was washed with hydrochloric acid and then with an aqueous sodium bicarbonate solution, and concentrated by removal of the solvent under reduced pressure. The residue was distilled under reduced pressure to obtain 1-chloro-7,9-dodecadiene (EZ/EE/(ZE+ZZ)=75.4/21.1/3.5, 31.85 g, 0.159 mol) mainly in an (E,Z) form. The yield was 79.3%. The isomerization of conjugated double bonds was suppressed to about 9%. The structure was determined by nuclear magnetic resonance spectrum and mass spectrum.

Example 4

The 7,9-dodecadien-1-ol (EZ/EE/(ZE+ZZ)=84.6/14.2/1.2, 36.46 g, 0.200 mol) comprising mainly an (E,Z) isomer, tributylamine (68.09 g, 0.360 mol) and N,N-dimethylformamide (60 g) were placed in a reaction vessel, and stirred at 5 to 10° C. for 30 minutes. After stirring, methanesulfonyl chloride (32.07 g, 0.280 mol) was added dropwise thereto at 5 to 15° C. After completion of the dropwise addition, the reaction mixture was stirred at 60 to 65° C. for 2 hours. Then, water (100 g) was added to the reaction mixture to terminate the reaction thereof. Hexane (100 g) was added thereto to separate the reaction mixture into phases. The organic phase was washed with hydrochloric acid and then with an aqueous sodium bicarbonate solution, and concentrated by removal of the solvent under reduced pressure. The residue was distilled under reduced pressure to obtain 1-chloro-7,9-dodecadiene (EZ/EE/(ZE+ZZ)=78.1/18.5/3.4, 31.73 g, 0.158 mol) mainly in an (E,Z) form. The yield was 79.2%. The isomerization of conjugated double bonds was suppressed to about 7%. The structure was determined by nuclear magnetic resonance spectrum and mass spectrum.

Example 5

The 7,9-dodecadien-1-ol (EZ/EE/(ZE+ZZ)=84.6/14.2/1.2, 36.46 g, 0.200 mol) comprising mainly an (E,Z) isomer, triethylamine (36.43 g, 0.360 mol) and N,N-dimethylformamide (60 g) were placed in a reaction vessel, and stirred at 5 to 10° C. for 30 minutes. After stirring, methanesulfonyl chloride (32.07 g, 0.280 mol) was added dropwise thereto at 5 to 15° C. After completion of the dropwise addition, the reaction mixture was stirred at 60 to 65° C. for 8 hours. Then, water (100 g) was added to the reaction mixture to terminate the reaction thereof. Hexane (100 g) was added thereto to separate the reaction mixture into phases. The organic phase was washed with hydrochloric acid and then with an aqueous sodium bicarbonate solution, and concentrated by removal of the solvent under reduced pressure. The residue was distilled under reduced pressure to obtain 1-chloro-7,9-dodecadiene (EZ/EE/(ZE+ZZ)=78.0/18.4/3.6, 17.34 g, 0.0864 mol) mainly in an (E,Z) form. The yield was 43.2%. The isomerization of conjugated double bonds was suppressed to about 7%. The structure was determined by nuclear magnetic resonance spectrum and mass spectrum.

Example 6

The 7,9-dodecadien-1-ol (EZ/EE/(ZE+ZZ)=84.6/14.2/1.2, 36.46 g, 0.200 mol) comprising mainly an (E,Z) isomer, pyridine (28.48 g, 0.360 mol) and N,N-dimethylformamide (60 g) were placed in a reaction vessel, and stirred at 5 to 10° C. for 30 minutes. After stirring, p-toluenesulfonyl chloride (53.38 g, 0.280 mol) was added dropwise thereto at 5 to 15° C. After completion of the dropwise addition, the reaction mixture was stirred at 60 to 65° C. for 2 hours. Then, water (100 g) was added to the reaction mixture to terminate the reaction thereof. Hexane (100 g) was added thereto to separate the reaction mixture into phases. The organic phase was washed with hydrochloric acid and then with an aqueous sodium bicarbonate solution, and concentrated by removal of the solvent under reduced pressure. The residue was distilled under reduced pressure to obtain 1-chloro-7,9-dodecadiene (EZ/EE/(ZE+ZZ)=83.1/15.0/1.9, 33.57 g, 0.167 mol) mainly in an (E,Z) form. The yield was 83.6%. The isomerization of conjugated double bonds was suppressed to about 2%. The structure was determined by nuclear magnetic resonance spectrum and mass spectrum.

Example 7

The 7,9-dodecadien-1-ol (EZ/EE/(ZE+ZZ)=84.6/14.2/1.2, 36.46 g, 0.200 mol) comprising mainly an (E,Z) form, pyridine (28.48 g, 0.360 mol) and N,N-dimethylformamide (60 g) were placed in a reaction vessel, and stirred at 5 to 10° C. for 30 minutes. After stirring, benzenesulfonyl chloride (49.45 g, 0.280 mol) was added dropwise thereto at 5 to 15° C. After completion of the dropwise addition, the reaction mixture was stirred at 60 to 65° C. for 2 hours. Then, water (100 g) was added to the reaction mixture to terminate the reaction thereof. Hexane (100 g) was added thereto to separate the reaction mixture into phases. The organic phase was washed with hydrochloric acid and then with an aqueous sodium bicarbonate solution, and concentrated by removal of the solvent under reduced pressure. The residue was distilled under reduced pressure to obtain 1-chloro-7,9-dodecadiene (EZ/EE/(ZE+ZZ)=84.3/14.1/1.6, 31.26 g, 0.156 mol) mainly in an (E,Z) form. The yield was 77.9%. The isomerization of conjugated double bonds was suppressed to about 0.5%. The structure was determined by nuclear magnetic resonance spectrum and mass spectrum.

Example 8

The 9,11-tetradecadien-1-ol (ZE/EE/(EZ+ZZ)=87.5/11.8/0.7, 42.07 g, 0.200 mol) comprising mainly a (Z,E) isomer, pyridine (28.48 g, 0.360 mol) and N,N-dimethylformamide (60 g) were placed in a reaction vessel, and stirred at 5 to 10° C. for 30 minutes. After stirring, methanesulfonyl chloride (32.07 g, 0.280 mol) was added dropwise thereto at 5 to 15° C. After completion of the dropwise addition, the reaction mixture was stirred at 60 to 65° C. for 2 hours. Then, water (100 g) was added to the reaction mixture to terminate the reaction thereof. Hexane (100 g) was added thereto to separate the reaction mixture into phases. The organic phase was washed with hydrochloric acid and then with an aqueous sodium bicarbonate solution, and concentrated by removal of the solvent under reduced pressure. The residue was distilled under reduced pressure to obtain 1-chloro-9,11-tetradecadiene (ZE/EE/(EZ+ZZ)=85.4/12.9/1.7, 41.14 g, 0.180 mol) mainly in a (Z,E) form. The yield was 89.9%. The isomerization of conjugated double bonds was suppressed to about 2%.

[Nuclear magnetic resonance spectrum] $^1$H-NMR (300 MHz, CDCl$_3$): δ1.02 (3H, t), 1.28-1.46 (10H, m), 1.76 (2H, tt), 2.08-2.20 (4H, m), 3.53 (2H, t), 5.30 (1H, dt), 5.70 (1H, dt), 5.95 (1H, dd), 6.30 (1H, dd); $^{13}$C-NMR (75.6 MHz, CDCl$_3$): δ13.20, 25.32, 26.28, 27.04, 28.25, 28.53, 28, 73, 29.08, 32.07, 44.51, 124.08, 128.09, 128.82, 135.45

[Mass spectrum] EI-mass spectrum (70 eV): m/z 228 (M$^+$), 95, 82, 67, 55, 41, 29

Example 9

The 8,10-dodecadien-1-ol (EE/(ZE+EZ+ZZ)=95.3/4.7, 36.46 g, 0.200 mol) comprising mainly an (E,E) isomer, pyridine (28.48 g, 0.360 mol) and N,N-dimethylformamide (60 g) were placed in a reaction vessel, and stirred at 5 to 10° C. for 30 minutes. After stirring, methanesulfonyl chloride (32.07 g, 0.280 mol) was added dropwise thereto at 5 to 15° C. After completion of the dropwise addition, the reaction mixture was stirred at 60 to 65° C. for 2 hours. Then, water (100 g) was added to the reaction mixture to terminate the reaction thereof. Hexane (100 g) was added thereto to separate the reaction mixture into phases. The organic phase was washed with hydrochloric acid and then with an aqueous sodium bicarbonate solution, and concentrated by removal of the solvent under reduced pressure. The residue was distilled under reduced pressure to obtain 1-chloro-8,10-dodecadiene (EE/(ZE+EZ+ZZ)=96.3/3.7, 35.72 g, 0.178 mol) mainly in an (E,E) form. The yield was 88.9%. The isomerization of conjugated double bonds was suppressed to about 1%.

[Nuclear magnetic resonance spectrum] $^1$H-NMR (300 MHz, CDCl$_3$): δ1.31 (3H, t), 1.32-1.48 (6H, m), 1.71-1.80 (4H, m), 2.04 (2H, dt), 3.52 (2H, t), 5.50-5.62 (2H, m), 5.95-6.70 (2H, m); $^{13}$C-NMR (75.6 MHz, CDCl$_3$): δ17.97, 26.80, 28.71, 28.94, 29.27, 32.46, 32.59, 45.09, 126.72, 130.31, 131.65, 131.92

[Mass spectrum] EI-mass spectrum (70 eV): m/z 200 (M$^+$), 95, 81, 68, 55, 41, 27

Example 10

The 3,5-pentadecadien-1-ol (EZ/EE/(ZE+ZZ)=86.1/11.4/2.4, 44.87 g, 0.200 mol) comprising mainly an (E,Z) isomer, pyridine (22.15 g, 0.280 mol) and N,N-dimethylformamide (60 g) were placed in a reaction vessel, and stirred at 5 to 10° C. for 30 minutes. After stirring, methanesulfonyl chloride (27.49 g, 0.240 mol) was added dropwise thereto at 5 to 10° C. After completion of the dropwise addition, the reaction mixture was stirred at 60° C. for 4 hours. Then, water (100 g) was added to the reaction mixture to terminate the reaction thereof. Hexane (100 g) was added thereto to separate the reaction mixture into phases. The organic phase was washed with hydrochloric acid and then with an aqueous sodium bicarbonate solution, and concentrated by removal of the solvent under reduced pressure. The residue was distilled under reduced pressure to obtain 1-chloro-3,5-pentadecadiene (EZ/EE/(ZE+ZZ)=84.3/13.2/2.4, 46.38 g, 0.191 mol) mainly in an (E,Z) form. The yield was 95.3%. The isomerization of conjugated double bonds was suppressed to about 2%.

[Nuclear magnetic resonance spectrum] $^1$H-NMR (300 MHz, CDCl$_3$): δ0.884 (3H, t), 1.21-1.34 (14H, m), 2.16 (2H, dt), 2.57 (2H, dt), 5.40 (1H, dt), 5.63 (1H, dt), 5.96 (1H, dd), 5.41 (1H, dd); $^{13}$C-NMR (75.6 MHz, CDCl$_3$): δ14.09, 22.67, 27.73, 29.24, 29.32, 29.50, 29.63, 29.69, 31.88, 36.06, 44.00, 127.87, 128.55, 128.84, 132.03

[Mass spectrum] EI-mass spectrum (70 eV): m/z 242 (M$^+$), 116, 81, 67, 55, 41, 29

Comparative Example 1

The 7,9-dodecadien-1-ol (EZ/EE/(ZE+ZZ)=84.6/14.2/1.2, 36.46 g, 0.200 mol) comprising mainly an (E,Z) isomer, triethylamine (20.24 g, 0.200 mol) and toluene (63 g) were placed in a reaction vessel, and stirred at 5 to 10° C. for 10 minutes. After stirring, thionyl chloride (25.70 g, 0.216 mol) was added dropwise thereto at 5 to 20° C. After completion of the dropwise addition, the temperature of the reaction mixture was increased slowly to 60° C. over 3 hours. After increase of the temperature, the reaction mixture was stirred at 60 to 65° C. for 2 hours. The reaction mixture was then cooled. Subsequently, an aqueous 25% by weight sodium hydroxide solution (71 g) and water (68 g) were added thereto to terminate the reaction thereof. Hexane was added thereto to separate the reaction mixture into phases, and concentrated by removal of the solvent under reduced pressure. The residue was distilled under reduced pressure to obtain 1-chloro-7,9-dodecadiene (EZ/EE/(ZE+ZZ)=59.1/31.6/9.3, 36.12 g, 0.180 mol) mainly in an (E,Z) form. The yield was 90%.

Thus, when chlorination was conducted using thionyl chloride as a chlorinating agent, the isomerization of conjugated double bonds increased to about 25%. The structure was determined using nuclear magnetic resonance spectrum and mass spectrum.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed.

The invention claimed is:
1. A method for producing a chlorohydrocarbon having conjugated double bonds, the method comprising a step of chlorinating an alcohol having conjugated double bonds with a chlorinating agent in a solvent in the presence of a base and in the absence of metal salt for chlorination of the alcohol, wherein the alcohol is of the following formula (1):

RCH═CHCH═CH—Z—OH     (1)

wherein R is a hydrogen atom, a linear $C_{1-17}$, a branched $C_{1-17}$ or a cyclic $C_{3-17}$ monovalent hydrocarbon group which may have at least one double bond or at least one triple bond; and Z represents a linear $C_{2-17}$, a branched $C_{2-17}$ or a cyclic $C_{3-17}$ divalent hydrocarbon group which may have at least one double bond or at least one triple bond, wherein the chlorinating agent is a sulfonyl chloride and the base is pyridine, wherein the chlorination reaction is substantially stereoselective, and wherein the amount of isomerization of the chlorohydrocarbon having conjugated double bonds is less than 10%.

* * * * *

UNITED STATES PATENT AND TRADEMARK OFFICE
CERTIFICATE OF CORRECTION

PATENT NO. : 9,845,273 B2
APPLICATION NO. : 14/189373
DATED : December 19, 2017
INVENTOR(S) : Miyake et al.

It is certified that error appears in the above-identified patent and that said Letters Patent is hereby corrected as shown below:

In the Specification

Column 7, Line 29: Please correct "28, 73," to read -- 28.73 --

Signed and Sealed this
Nineteenth Day of June, 2018

Andrei Iancu
*Director of the United States Patent and Trademark Office*